US005186938A

United States Patent [19]

Sablotsky et al.

[11] Patent Number: 5,186,938

[45] Date of Patent: Feb. 16, 1993

[54] ADHESIVE TRANSDERMAL DOSAGE LAYER

[75] Inventors: Steven Sablotsky, Miami, Fla.; John M. Questel, Cuyahoga Falls; James A. Thompson, Akron, both of Ohio

[73] Assignee: Key Pharmaceuticals, Inc., Kenilworth, N.J.

[21] Appl. No.: 744,632

[22] Filed: Aug. 7, 1991

Related U.S. Application Data

[63] Continuation of Ser. No. 515,771, Apr. 29, 1990, abandoned, which is a continuation of Ser. No. 290,824, Dec. 22, 1988, abandoned, which is a continuation of Ser. No. 758,233, Jul. 24, 1985, abandoned, which is a continuation-in-part of Ser. No. 633,992, Jul. 24, 1984, abandoned.

[51] Int. Cl.$^5$ .............................................. A61F 13/00

[52] U.S. Cl. .................................... 424/443; 424/448; 424/449; 424/447

[58] Field of Search ....................... 424/449, 448, 447; 427/385.5

[56] References Cited

U.S. PATENT DOCUMENTS

| | | | |
|---|---|---|---|
| 3,742,951 | 7/1973 | Zaffaroni | 424/448 |
| 3,896,789 | 7/1975 | Trancik | 424/448 |
| 4,310,509 | 1/1982 | Berglund et al. | 424/448 |
| 4,374,164 | 2/1983 | Blank | 427/385.5 |
| 4,390,530 | 6/1983 | Nagai et al. | 424/449 |
| 4,421,737 | 12/1983 | Ito et al. | 424/449 |
| 4,482,534 | 11/1984 | Blank | 424/449 |
| 4,608,249 | 8/1986 | Otsuka et al. | 424/448 |

FOREIGN PATENT DOCUMENTS 55-2604 1/1981 Japan .

*Primary Examiner*—Thurman K. Page
*Assistant Examiner*—Leon R. Horne
*Attorney, Agent, or Firm*—John J. Maitner; Eric S. Dicker

[57] ABSTRACT

An adhesive bilayer transdermal dosage system capable of sustained release of a pharmaceutically active drug to the skin of a human patient having a first component layer which is a pharmaceutically active drug-containing essentially planar sheet of an at least partially cross-linked acrylic adhesive. The planar sheet is formed of a flexible self-supporting cross-linked acrylate of sufficient adhesivity, durability and strength whereby intimate diffusional contact with the skin of the patient is maintained for a period of at least about 24 hours without destruction of the physical integrity of the sheet. The sheet is capable of retaining, dispersed therein, sufficient pharmaceutically active drug to deliver to the skin a pharmaceutically effective amount of the drug over a 24-hour period without dissolution of the at least partially crosss-linked acrylic adhesive. The system also contains a second component layer intimately adhered to one side of the first component layer. The second component layer is resistant to the passage of the pharmaceutically active drug from the first component layer. Methods for making the first component layer and dosage system are also disclosed.

19 Claims, No Drawings

ADHESIVE TRANSDERMAL DOSAGE LAYER

REFERENCE TO RELATED APPLICATION

This is a continuation of application Ser. No. 07/515,771 filed Apr. 24, 1990, and now abandoned which is a continuation, of application Ser. No. 290,824 filed Dec. 22, 1988 now abandoned which is a continuation, of application Ser. No. 758,233 filed Jul. 24, 1985 now abandoned which application is a continuation-in-part of copending application Ser. No. 633,992 filed Jul. 24, 1984, abandoned.

FIELD OF THE INVENTION

The present invention relates to an adhesive transdermal dosage layer capable of sustained release of a pharmaceutically active drug to the skin of a human patient. Moreover, the invention relates to a bilayer dosage form containing a first component layer formed of a cross-linked acrylate polymer having a pharmaceutically active drug dispersed and intimately intermixed therein and a second component layer intimately adhered to a surface of the first component layer, the pharmaceutically active drug present in such an amount, and interacting with the cross-linked acrylate polymer in such a manner, that adhesive properties are maintained.

BACKGROUND OF THE INVENTION

It is well known that many drugs, if taken orally, are destroyed on the first pass through the liver. It is also well known that when many drugs are taken orally, their rate of absorption into the system is not constant. In view of such difficulties, a number of different drug delivery systems have been developed. Recently, the use of transdermal delivery systems has met with increasing interest by researchers in the pharmaceutical drug-delivery field.

In attempting to produce the invention described in detail infra, the inventors incorporated a pharmaceutically active drug (nitroglycerin) into an acrylic adhesive in order to form a transdermal drug delivery system. After incorporating the drug into the adhesive polymer, the inventors found that the adhesive dissolved. Accordingly, the structural integrity of the dosage unit formed was lost and the rate of release of the nitroglycerin therefrom could not be controlled. Since the dissolution of the adhesive appeared to be caused by the incorporation of the nitroglycerin, the inventors decreased the amount of nitroglycerin in order to maintain the structural integrity of the adhesive and prevent it from dissolving. The inventors found that, by decreasing the amount of nitroglycerin in the adhesive, dissolution could be prevented and a transdermal delivery system could be prepared. However, such a system contained a relatively small amount of nitroglycerin. Accordingly, when the system was applied to human skin, although the adhesive properties of the system were maintained, the release of nitroglycerin was so slight as to not have the desired effect on the patient to which the system was applied. The inventors have since found that others apparently attempted the same procedure and also found that the amount of nitroglycerin released was not sufficient or not controllable due to dissolution (see Ito, et al. in U.S. Pat. No. 4,421,737, column 7, line 68—column 8, line 2; Canadian Patent 1,144,070, page 14, lines 3-5, and U.S. Pat. No. 4,420,470 at column 1, lines 23-34.)

In an attempt to solve the above-referred to problems, the inventors tried various types and combinations of adhesive polymers without success. The inventors found that with certain polymers and combinations thereof, the polymer composition formed was simply too hard and insoluble with respect to the solvent-acting drug such as nitroglycerin. Accordingly, the polymer composition did not have sufficient adhesive properties in order to adhere firmly to human skin and could not incorporate therein a sufficient amount of the solvent-acting drug such as nitroglycerin. Other polymer compositions that did have sufficient adhesive properties could not maintain their structural integrity when standing alone or when exposed to human skin and body heat over a substantial period of time and further became dissolved when sufficient amounts of nitroglycerin were incorporated therein. The present inventors found that these problems could be solved by including within the composition a cross-linking agent in a relatively small amount. The cross-linked adhesives disclosed in U.S. Pat. Nos. 4,374,164 and 3,475,363 are useful in connection with the present invention and these patents are incorporated herein by reference for purposes of disclosing such cross-linked adhesives.

The inventors noted that by including large amounts of cross-linking agents into polymer compositions that included solvent-acting drugs incorporated therein, the adhesive properties of the compositions were lost, i.e., the composition lost its tackiness. If insufficient amounts of cross-linking agent were included in the composition, the composition was dissolved.

DISCUSSION OF THE PRIOR ART

U.S. Pat. No. 4,294,820 to Keith, et al. discloses a polymer diffusion matrix that allows for the transdermal delivery of phenylephrine. Keith, et al. have also utilized a matrix-type system for the transdermal delivery of other pharmaceutically active drugs such as terbutaline (as disclosed in U.S. Pat. No. 4,292,302) and clonidine (as disclosed in U.S. Pat. No. 4,292,303). A transdermal nitroglycerin delivery system is disclosed by Sanvordeker, et al. in U.S. Pat. No. 4,336,243 that involves the use of a silicon matrix. Keith, et al. disclosed the use of their matrix for the transdermal delivery of nitroglycerin in U.S. Pat. No. 4,291,015.

Prior art drug-delivery systems such as those mentioned above have various disadvantages including being difficult and expensive to manufacture and cumbersome and messy for the patient to use. In an attempt to simplify such systems, Striker, et al. formulated a transdermal release system that involves incorporating a pharmaceutically active substance directly into an adhesive material such as a skin-compatible polyacrylate; see U.S. Pat. No. 4,409,206. The patent discloses that a number of different pharmaceutically active drugs such as nitroglycerin can be incorporated in the adhesive material (see column 4, line 5). However, due to the properties of the adhesive materials used, the manner in which those properties are acted on by some pharmaceutically active drug compositions, and the method of incorporating such active drugs into the adhesives, the Striker, et al. transdermal release system does not allow for the incorporation of a large percentage of pharmaceutically active drug into the adhesive. Accordingly, the adhesive is likely to contain an insufficient amount of the pharmaceutically active drug to allow delivery of a pharmaceutically effective amount of the drug to a patient via transdermal delivery.

Hidetaka, et al. (in U.S. Pat. No. 4,390,520) also disclosed the incorporation of a pharmaceutically active drug (indomethacin) into a pressure-sensitive adhesive layer in order to form a transdermal delivery system. Although the system disclosed may be easier and more economical to manufacture than other transdermal delivery systems, the patent contains no information with respect to how it is possible to incorporate relatively large amounts of an organic solvent-acting pharmaceutically active drug into an adhesive without deteriorating its adhesive properties.

U.S. Pat. No. 4,420,470 discloses the incorporation of isosorbide dinitrate or pentaerythritol tetranitrate into an acryl-based copolymer having a particular glass transition temperature.

In U.S. Pat. No. 4,310,509, Berglund, et al. disclose the incorporation of a broad-spectrum antimicrobial agent into a pressure-sensitive adhesive and mention that the adhesive components may include various chemical modifiers such as tackifiers, cross-linkers, stabilizers, initiators, etc. (see column 3, lines 18-57). The Berglund, et al. invention is directed to the development of a pressure-sensitive adhesive composition that is "substantially free of acidic components" in order to facilitate the homogeneous dispersion of the antimicrobial agents without any negative alteration to their activity. The invention appears merely to deliver the antimicrobial agents to the skin for their topical antibacterial effect thereon. Accordingly, the disclosure is directed to maintaining the properties of the pressure-sensitive adhesive so that those properties do not have an undesirable effect on the activity of the antimicrobial agents. Berglund, et al. do not disclose how to incorporate a relatively large amount of an organic solvent-acting pharmaceutically active drug into an adhesive without deteriorating its adhesive properties.

SUMMARY OF THE INVENTION

The present invention relates to an adhesive transdermal dosage layer that can contain relatively large quantities of a pharmaceutically active drug in the adhesive layer without causing any deterioration of the adhesive properties. The adhesive layer contains a dermatologically acceptable cross-linked adhesive acrylate polymer having intimately intermixed therein a pharmaceutically effective amount of a pharmaceutically active drug which, by itself or as dissolved in a solvent, acts as a solvent with respect to the adhesive acrylate polymer. The adhesive polymer or polymer combinations used may have good adhesive properties and compatibility with respect to human skin when used alone. However, these properties are adversely affected by the addition of either a pharmaceutically active drug such as nitroglycerin alone or a cross-linking agent alone. More specifically, by including nitroglycerin or any pharmaceutically active drug composition that acts as an organic solvent by itself or as dissolved in a solvent into the adhesive polymers, the polymers are dissolved to a certain extent causing a loss of structural integrity of the system formed of the adhesive polymers. If the solvent-acting drug remains incorporated in the polymers, the polymers become soft and runny and will not form a structure necessary for producing the desired drug delivery system. Alternatively, if a cross-linking agent alone is incorporated in the adhesive polymers, the polymers lose their tackiness and the structure will no longer adhere to human skin. (Hereinafter, solvent-acting pharmaceutically active drugs and pharmaceutically active drugs dissolved in solvents will be referred to as "solvent-acting drugs".) Thus, the present invention requires the combined presence of the adhesive acrylate polymer, the pharmaceutically active drug, and the cross-linking agent.

Applicants have found that it is possible to prepare an adhesive transdermal dosage layer containing significantly large dosages of a pharmaceutically active drug (such as nitroglycerin) by intimately mixing an adhesive acrylate polymer (defined in more detail infra), a pharmaceutically active drug, and a cross-linking agent for the carylate polymer. The cross-linking agent is added after the adhesive acrylate polymer and the pharmaceutically active drug are mixed thoroughly. The resulting layer, which retains its adhesive characteristics, will have the drug mixed therein in a quantity that facilitates transdermal application of the drug.

A second component layer (or facing layer) is attached to the adhesive transdermal dosage layer to form an adhesive bilayer transdermal dosage system that can be applied to the skin. This second component layer is different from a conventional release layer that may be attached to the adhesive bilayer transdermal dosage system. The release layer is removed before application of the adhesive bilayer transdermal dosage system to the skin.

The present inventors have found that by combining solvent-acting drugs and cross-linking agents with adhesive acrylate polymers, it is possible to incorporate the solvent-acting drugs in the polymers in relatively large amounts without adversely affecting the desirable properties of the polymers.

OBJECTS OF THE INVENTION

It is an object of the present invention to provide an adhesive transdermal dosage system for the sustained release of a pharmaceutically active drug to the skin of a human patient, the dosage system containing a first component layer that is a pharmaceutically active drug containing essentially planar sheet of an at least partially cross-linked acrylate adhesive, the essentially planar sheet comprising a flexible self-supporting cross-linked acrylate polymer of sufficient adhesivity, durability, and strength where the skin of the patient can be maintained in intimate diffusional contact therewith, the layer capable of retaining a quantity of pharmaceutically active drug over a period of 24 hours without destruction of the physical integrity of the sheet, the essentially planar sheet being capable of retaining dispersed therein sufficient pharmaceutically active drug to deliver to the skin a pharmaceutically effective amount of the pharmaceutically active drug up to a 24-hour or more time interval, without dissolution of the at least partially cross-linked acrylate polymer adhesive, and a second component layer intimately adhered to one side of the first component layer, the second component layer being resistant to the passage of the pharmaceutically active drug from the first component layer.

Another object of the invention is to provide a dosage system further having a release liner placed over the first component layer on a surface opposite the second component layer, the release liner being resistant to the passage of a pharmaceutically active drug from the first component layer. The release liner is removed from the system when it is applied to a patient.

Still another object of the invention is to provide a dosage system wherein nitroglycerin is delivered to the skin in an amount of from about 0.3 to about 0.7 mg per square centimeter of the first component layer per 24-hour time interval.

Yet another object of the invention is to provide a dosage system wherein isosorbide dinitrate is delivered to the skin in an amount of from about 0.1 to about 0.3 mg per square centimeter of the first component layer per 24-hour time interval.

Another object of the invention is to provide an adhesive transdermal dosage system containing a large quantity of pharmaceutically active drug so that there is always an adequate supply of the drug for passage through the human skin, which is the rate controlling agent.

These and other objects of the invention will become apparent to those skilled in the art upon reading the following detailed description.

DETAILED DESCRIPTION OF THE INVENTION

The present inventors have developed an adhesive transdermal dosage system for the sustained release of a pharmaceutically active drug to the skin of a human patient. The dosage system has a first component layer which is a cross-linked acrylate polymer having a pharmaceutically active drug intimately dispersed therein and a second component layer that is intimately adhered to a surface of the first component layer.

The first component layer is a pharmaceutically active drug-containing planar sheet of an at least partially cross-linked pressure-sensitive acrylate adhesive. The planar sheet is a flexible, self-supporting, cross-linked acrylate polymer of sufficient adhesivity, durability, and strength whereby intimate diffusional contact with the skin of the patient is maintained for a period of at least 24 hours without destruction of the physical integrity of the sheet. The planar sheet is capable of retaining dispersed therein sufficient pharmaceutically active drug to deliver to the skin a pharmaceutically effective amount of the pharmaceutically active drug over a 24-hour time interval, without dissolution of the at least partially cross-linked acrylate adhesive. The pharmaceutically active drug is present in the adhesive in such an amount, and interacts with the adhesive in such a manner, that the adhesive properties are maintained and may be improved.

Various types of dermatologically-acceptable adhesive polymers can be used in connection with the invention but dermatologically-acceptable acrylic adhesive polymer compositions work particularly well.

The adhesives used in the present invention contain about 1 to about 5% by weight of acrylic acid, about 5 to about 20% by weight of a $C_4$ to $C_{12}$ alkyl acrylate which functions as an internal plasticizer. The adhesives can also contain about 15 to about 94% by weight of a chain extender monomer bearing ethylenic unsaturation such as ethyl methacrylate, methyl methacrylate, and ethyl acrylate.

The acrylic acid provides the necessary carboxylic group needed to effect reaction with the cross-linking agent.

Representative $C_4$ to $C_{12}$ alkyl acrylates include n-butyl acrylate, hexyl acrylate, 2-ethylbutyl acrylate, isooctyl acrylate, 2-ethylhexyl acrylate, decyl acrylate, and dodecyl acrylate. The presence of the relatively large side chains permits these materials to function as internal plasticizers.

Other representative chain extenders in addition to those mentioned previously include vinyl monomers such as vinyl acetate, vinyl propionate, vinyl butyrate, vinyl toluene, styrene, vinyl benzene and the like; hydroxy alkyl (meth)acrylates such as hydroxyethyl methacrylate, hydroxyethyl acrylate, hydroxypropyl methacrylate, and hydroxypropyl acrylate; polyalkylene glycol (meth)acrylates such as diethylene glycol monoacrylate, diethylene glycol monomethacrylate, dipropylene glycol monoacrylate, dipropylene glycol monomethacrylate, triethylene glycol monoacrylate, triethylene glycol monomethacrylate, tetraethylene glycol monoacrylate, and polyethylene glycol monoacrylate; acrylamide, methacrylamide, (meth)acrylonitrile, and the like. Chain extending monomers are well known in the art and other such monomers can be used as long as they can produce an adhesive having the characteristics required for use in the present invention.

The cross-linking agents useful in the present invention are those materials capable of reacting with the carboxyl groups of the acrylic acid components of the adhesive. Representative cross-linking agents include formaldehyde resins based on melamine such as methylol melamines and methylol ureas and divalent metallic salts such as zinc acetate. The cross-linking mechanism is a nucleophilic second order substitution.

The cross-linking agents are present in an amount of 0.2 to about 1% by weight based on the total weight of the first component layer.

As a specific example of a useful adhesive composition, the inventors have found that a butylacrylate copolymer having a molecular weight in the range of 2,000 to 1 million with a peak at 65,000 is particularly useful, especially when it contains 0.5% alkyl-substituted melamine with an emulsifying agent in combination with 36% weight water. The inventors have also found that a butylacrylate copolymer having a molecular weight in the range of 2,000 to 1 million with a peak at 47,000 is also particularly useful, especially when containing emulsifying agents in combination with 34% water. These copolymers may be combined with a thickener which is a copolymer composition that includes potassium polyacrylate and/or sodium polyacrylate. (Amsco-Res 6038 has been found to be a useful thickener.)

The adhesive polymer compositions of the invention are combined with a pharmaceutically active drug, e.g., a vasodilator such as nitroglycerin, which acts as a solvent with respect to the adhesives and then is combined with a cross-linking agent. The cross-linking agent may be comprised of about 81% trialkyl melamine derivative, about 10% water, and about 9% methanol. The cross-linking agent as a whole is present in the composition in an amount in the range of 0.2 to 1% by weight based on the total weight of the composition including adhesive polymer, pharmaceutically active drug, and cross-linking agent. The effects of cross-linkers are discussed in U.S. Pat. No. 4,374,164 referred to above. The melamine derivative may be a melamine-formaldehyde polymer formed in the presence of excess formaldehyde resulting in the presence of groups that will readily react with carboxyl groups in the acrylic acid portion of the adhesive.

As indicated above, the dosage unit of the present invention might have any solvent-acting drug incorporated therein. In its preferred form, the drug is a vasodilator. More specifically, the vasodilators are nitrate esters (—C—O—$NO_2$) characterized by a sequence of carbon-oxygen-nitrogen and nitrite esters characterized by a (—C—O—NO) sequence. Nitro compounds (which are not vasodilators) possess carbon-nitrogen bonds ($C—NO_2$). Thus, glyceryl trinitrate is not a nitro compound, and it is erroneously called nitroglycerin; however, this nomenclature is both widespread and official. Preferred embodiments of the invention include solids of mannitol hexanitrate, erythritol tetranitrate, pentaerythritol tetranitrate and/or isosorbide dinitrate dissolved in a solvent and incorporated in the cross-linked adhesive. The most preferred embodiment is nitroglycerin incorporated in the cross-linked adhesive and especially incorporated in an amount of about 20 to 50 or 60% by weight based on the weight of the first component layer.

By adjusting the type and amount of adhesive polymer, vasodilator, and cross-linking agent, it is possible to produce an adhesive composition that can be effectively utilized as a transdermal drug delivery system. The interacting effects of the solvent-acting vasodilator and cross-linking agent make it possible to improve the stability, adhesion, wear and amount of drug delivery per unit area.

In order to be useful in the invention, the acrylic adhesives must be dermatologically acceptable since the dosage system of the invention is to be applied to human skin. Further, the acrylic composition utilized must be sufficiently adhesive so as to firmly adhere to human skin, even when subjected to certain adverse conditions such as humidity, movement and showers and/or bathing, but not be so adhesive as to cause irritation to the skin or substantial discomfort to the patient when removed from the skin. Further, the adhesives used must be compatible with the solvent-acting drug used.

Once the mixture of the acrylic adhesive polymer and the pharmaceutically active drug is formed, it must be combined with a cross-linking agent for use in connection with the present invention. The inventors have found that active derivatives of trialkyl melamine are useful cross-linkers when used in combination with copolymers containing a butylacrylate component. (See U.S. Pat. No. 4,374,164 wherein the alkyl is isobutyl forming isobutylated melamine.) When utilizing trialkyl melamine derivatives in combination with the butylacrylate copolymer, the cross-linking agent is preferably present in an amount in the range of 0.3 to 0.8% by weight and particularly preferably 0.4% by weight. It is known that very small amounts of cross-linking agents can have a substantial effect on the properties of the polymers. U.S. Pat. No. 3,520,806 is incorporated herein by reference with respect to its disclosure of cross-linking agents and the amounts necessary in order to produce a cross-linked polymer.

The inclusion of the cross-linking agent in the acrylic adhesive allows the system to maintain its structural integrity even in the presence of the solvent-acting drugs. The cross-linking agent causes the formation of a three-dimensional molecular lattice network. The formation of such a network distinguishes the cross-linked adhesives disclosed herein from acrylic adhesives used in the prior art.

It is preferable in the present invention to include a thickener in a first component layer comprised of the cross-linked acrylic adhesive and solvent-acting drug. Although it is believed that various thickeners that would be known to those skilled in the art could be used, the present inventors have found it particularly useful to include a thickener which is a copolymer of potassium polyacrylate and a lesser amount of an hydroxyalkyl acrylate. Such a thickener is sold by Union 76 under the trade name Amsco-Res 6038. The thickener should be chosen and included in an amount so as to allow for the creation of a smooth composition and good distribution of the throughout the cross-linked acrylic adhesive. The thickener is generally present in an amount in the range of 0.9 to about 1.4% by weight and more preferably in an amount of 1.0% by weight.

The second (or facing) layer is a backing layer for preventing the escape of active ingredients from the first layer. However, the second layer should not absorb the active ingredient and act as a "sink" for the active ingredient. The second layer is desirably oxygen-permeable, but may be an occlusive material such as metal foil (e.g. aluminum), polyolefin (e.g. polyethylene or polypropylene), polyester (e.g. polyethylene terephthalate), and polyamide (e.g. nylon), as described in U.S. Pat. No. 4,291,015, the disclosure of which is incorporated by reference.

EXAMPLE

| COMPONENT | Target | Range |
|---|---|---|
| Acrylic Pressure-Sensitive Adhesive (Monsanto RA-3011)[1] | 30.2 | 27–35 |
| Acrylic Pressure-Sensitive Adhesive (Monsanto RA-2397)[2] | 30.2 | 27–35 |
| Nitroglycerin[3] | 33.4 | 30.0–38.4 |
| Thickener (Union 78 Amsco-Res 6038)[4] | 1.2 | .9–1.8 |
| Cross-linking Agent (American Cyanamid Aerotex Resin 3730)[5] | .4 | .2–.8 |
| Water | 4.0 | up to 10 |
| | 100.00% | |

[1]Butyl acrylate copolymer (MW 2,000–1,000,000, peak at 65,000) with 0.5% alkyl substituted melamine with emulsifier (36% water.)
[2]Butyl acrylate copolymer (MW 2,000–1,000,000, peak at 47,000) with emulsifier (34% water.)
[3]The amount of pure nitroglycerin after any solvent is taken off.
[4]13% copolymer - sodium polyacrylate.
[5]81% trialkyl melamine derivative, 10% water, 9% MeOH.

The dosage system of the present invention can be produced in a number of ways. It is particularly important to form the first component layer in a series of steps using sufficient agitation, at each step, so as to avoid coagulation and clumping together of any of the components. After the first component layer is formed, the composition making up this layer can be placed in contact with the second component layer in any manner known to those skilled in the art in order to produce the bilayer transdermal dosage system.

The bilayer transdermal dosage system can be produced as follows:

(1) appropriate amounts of one or more acrylic adhesives are combined and mixed thoroughly together in a vessel;

(2) the mixed adhesives are then mixed with an appropriate amount of purified water until a homogeneous mixture of the adhesives and water is obtained;

(3) a thickener is then added to the water-adhesive mixture and agitated to form a smooth homogeneous mixture;

(4) the homogeneous mixture is then transferred to a vessel where a pharmaceutically active drug such as nitroglycerin can be added;

(5) the pharmaceutically active drug is then added to the homogeneous mixture and agitation is carried out until the mixture and the pharmaceutically active drug form a smooth homogeneous mix;

(6) the homogeneous mix containing the pharmaceutically active drug is then transferred to an adhesive mixing vessel;

(7) the mix containing the pharmaceutically active drug is then combined with a cross-linking agent and thoroughly agitated in order to cause cross-linking between the polymer chains of the pressure-sensitive adhesive;

(8) the cross-linked acrylic adhesive containing the pharmaceutically active drug is then transferred to a coating station;

(9) the cross-linked adhesive containing the pharmaceutically active drug is now in a form such that it makes up the first component layer of the invention and can be released onto a layer which will form the second component layer;

(10) when the first component layer has been placed onto the second layer, the bilayer system is then passed into a heating means in order to remove water and/or solvents which may have been included in the mixing procedure; and

(11) after the heating is completed and the solvents are removed, the first component layer will be firmly adhered to the second component layer and the system can be wound into rolls for storage; or alternatively

(12) the bilayer system is cut or punched into forms making up a bilayer transdermal dosage unit.

The dosage system may be cut into any desirable unit form. However, a circular form is particularly preferred as it contains no corners which might be easily detached from the skin. The amounts of each of the components can be particularly adjusted within the above-disclosed ranges by those skilled in the art in order to obtain the desired results. Some of the order of the steps, the amount of the ingredients, and the amount and time of agitation or mixing are important with respect to avoiding coagulation or clumping together of the components. These factors can be adjusted by those skilled in the art while keeping in mind the object of providing a smooth homogeneous mix. Other methods including changing some of the order of steps can be carried out and will give desirable results.

In addition to having various shapes, the dosage units produced may come in various sizes. A surface area in the range of 1 to 200 $cm^2$ is contemplated and the presently contemplated preferred sizes are 5, 10, 15, 20, 25 and 30 $cm^2$. The thickness may vary over a wide range but is preferably 2.5 to 5 mm and particularly preferably 3.5 to 4 mm thick. The present invention allows for the incorporation of enough pharmaceutically active drug such as nitroglycerin to provide efficacy with a dosage system having a 5 $cm^2$ surface area and a thickness of about 3.5 to 4 mm.

In the above referred-to steps, the acrylic adhesive was first formed and then had the nitroglycerin added to it in a pure form. In order to carry out such a procedure, the nitroglycerin must be added to the adhesive in an explosion-proof container. After adding the nitroglycerin to the adhesive, the mixture becomes stabilized and can be transported without danger. If bomb-proof facilities are not available for containing nitroglycerin in a pure form, then the bilayer transdermal dosage unit can be prepared by the following steps: (1) appropriate amounts of one or more acrylic adhesives are combined together and thoroughly mixed in a mixing vessel;

(2) the pressure-sensitive adhesives are combined with purified water in order to form a homogeneous mixture;

(3) the homogeneous mixture of water and adhesive is combined with a solution of nitroglycerin with ethanol (the nitroglycerin is present in the ethanol in a ratio of ethanol:nitroglycerin of 9:1) and the nitroglycerin solution and adhesive are thoroughly agitated together in order to form a homogeneous mix;

(4) the mix of nitroglycerin and adhesive is then treated in order to remove 85 to 95% of the ethanol;

(5) a thickener is added to the adhesive and agitated in order to form a smooth mixture;

(6) a cross-linking agent is added to the smooth mixture and thoroughly mixed in order to bring about crosslinking between the polymer chains of the adhesive; and (7) the cross-linked adhesive containing the nitroglycerin is now in a form which makes up the first component layer of the invention and can be transferred to a coating station.

As previously indicated, it is believed that the above method can be carried out in a variety of different ways in order to obtain the desired results. Modifications will be apparent to those skilled in the art. The immediately preceeding example included water in order to avoid "alcohol shock", i.e. destroying the stable emulsion resulting in coagulation of the polymers. Accordingly, water was added in the step (2) of the above referred-to method. Further, a thickener was added with step (3) of each of the above referred to methods prior to adding any nitroglycerin. (The thickener was added in order to provide a sufficiently high yield point for supporting the nitroglycerin as it migrates through the water into the polymer.)

The present invention has been disclosed and described herein in what is believed to be its most preferred embodiments. However, it is recognized that those skilled in the art will contemplate variations thereof which are not specifically disclosed herein. Accordingly, the scope of the present invention should not be construed as being limited to the above description.

What is claimed is:

1. An adhesive bilayer transdermal dosage system for the sustained release of nitroglycerin to the skin of a human patient, comprising:

(i) a first component layer formed of a nitroglycerin-containing essentially planar sheet of an at least partially cross-linked acrylic pressure-sensitive adhesive, said essentially planar sheet comprising a flexible self-supporting cross-linked acrylate polymer of sufficient adhesivity, durability and strength whereby intimate diffusional contact with skin of the patient is maintained for a period of at least about 24 hours without destruction of the physical integrity of said sheet, said essentially planar sheet being capable of retaining dispersed therein sufficient nitroglycerin to deliver to the skin a pharmaceutically effective amount of said nitroglycerin over a 24-hour time interval, without dissolution of the at least partially cross-linked acrylic pressure-sensitive adhesive and (ii) a second component layer intimately adhered to one side of said first component layer, said second component layer being resistant to the passage of pharmaceutically active drug from said first component layer;

wherein said first component layer comprises about 40 to about 80% by weight of acrylic adhesive; wherein said acrylic adhesive comprises about 1 to about 5% by weight of acrylic acid and about 5 to about 20% by weight of a $C_4$ to $C_{12}$ alkyl acrylate; about 20 to about 60% by weight of nitroglycerin; about 0.2 to about 1% of a cross-linking agent and 10% or less of water.

2. The adhesive bilayer transdermal dosage system of claim 1, further comprising:

a release line placed over said first component layer on a surface opposite said second component layer, the release liner being resistant to the passage of pharmaceutically active drug from said first component layer.

3. The adhesive bilayer transdermal dosage unit of claim 1, wherein said pharmaceutically active drug is nitroglycerin which is delivered to the skin in an amount of from about 0.3 to 0.7 mg per square centimeter of said first component layer per 24-hour time interval.

4. The adhesive bilayer transdermal dosage system of claim 1, wherein said first component layer contains about 40 to about 80% by weight of acrylic adhesive; about 20 to about 60% by weight of pharmaceutically active drug; about 0.2 to about 1% of a cross-linking agent and 10% or less of water.

5. The adhesive bilayer transdermal dosage system of claim 1, wherein said acrylic adhesive is present in an amount of about 54 to about 70% by weight.

6. The adhesive bilayer transdermal dosage system of claim 4, wherein said pharmaceutically active drug is a vasodilator.

7. The adhesive bilayer transdermal dosage system of claim 1 wherein said nitroglycerin and is present in an amount in the range of about 30 to about 38.4% by weight.

8. The adhesive bilayer transdermal dosage system of claim 1, wherein said cross-linking agent is a melamine derivative present in the amount in the range of about 0.3 to about 0.8% by weight.

9. The adhesive bilayer transdermal dosage system of claim 1 wherein said first component layer contains a thickener in an amount of about 0.9 to about 1.8% by weight.

10. The adhesive bilayer transdermal dosage system of claim 1, wherein said water is present in an amount of about 4% by weight, said acrylic adhesive is present in an amount of about 61.4% by weight, nitroglycerin is present in an amount of about 33.4% by weight, said cross-linking agent is present in an amount of 0.4% by weight, and said thickener is present in an amount of about 1.0% by weight.

11. The adhesive bilayer transdermal dosage system of claim 1, wherein said acrylate polymer contains about 1 to about 5% by weight of acrylic acid and about 5 to 20% by weight of a $C_4$ to $C_{12}$ alkyl acrylate.

12. An adhesive transdermal layer for the sustained release of a pharmaceutically active drug to the skin of a human patient, comprising:

a pharmaceutically active drug-containing essentially planar sheet of an at least partially cross-linked acrylic adhesive, said essentially planar sheet comprising a flexible self-supporting cross-linked acrylate polymer of sufficient adhesivity, durability and strength whereby intimate diffusional contact with skin of the patient is maintained for a period of at least about 24 hours without destruction of the physical integrity thereof, said essentially planar sheet being capable of retaining dispersed therein sufficient pharmaceutically active drug to deliver to the skin a pharmaceutically effective amount of said pharmaceutically active drug over a 24-hour time interval, without dissolution of the at least partially cross-linked acrylic pressure-sensitive adhesive.

13. The adhesive transdermal layer of claim 12, wherein said pharmaceutically active drug is a vasodilator.

14. The adhesive transdermal layer of claim 13, wherein said vasodilator is nitroglycerin.

15. The adhesive transdermal layer of claim 13, wherein said vasodilator is isosorbide dinitrate.

16. An adhesive transdermal layer for the sustained release of a pharmaceutically active drug formed by a) mixing an acrylic adhesive and water to form a homogeneous mixture;

b) adding a pharmaceutically active drug to said homogeneous mixture;

c) forming a smooth homogeneous mix of said pharmaceutically active drug and said homogeneous mixture;

d) adding a cross-linking agent for said acrylic adhesive to said smooth homogeneous mix;

e) undertaking cross-linking between said cross-linking agent and said acrylic adhesive; and f) removing sufficient water and solvent from the product of step e) to form said adhesive transdermal layer.

17. The adhesive transdermal layer of claim 1, wherein said pharmaceutically active drug is a vasodilator.

18. The adhesive transdermal layer of claim 17, wherein said vasodilator is nitroglycerin.

19. The adhesive transdermal layer of claim 18, wherein said nitroglycerin is present in an amount of 20 to 50% by weight based on said adhesive transdermal layer.

* * * * *

UNITED STATES PATENT AND TRADEMARK OFFICE

CERTIFICATE OF CORRECTION

PATENT NO. : 5,186,938 Page 1 of 2

DATED : Febuary 16, 1993

INVENTOR(S) : Steven Sablotsky, John M. Questel, and James A. Thompson

It is certified that error appears in the above-indentified patent and that said Letters Patent is hereby corrected as shown below:

On the Title page, item [56] References Cited, U.S. Patent Documents:

The Nagai et al. patent "4,390,530", should be numbered -- 4,390,520 --

| Column | Line | Correction |
|---|---|---|
| 3 | 1 | "Hidetaka", should be -- Nagai -- |
| 4 | 12 | "carylate", should be -- acrylate -- |
| 8 | 6 | after "of the", insert -- pharmaceutically active drug -- |
| 11 | 13 | "line", should be -- liner -- |
| 11 | 37 | after "nitroglycerin", delete -- and -- |

UNITED STATES PATENT AND TRADEMARK OFFICE

CERTIFICATE OF CORRECTION

PATENT NO. : 5,186,938

DATED : February 16, 1993

INVENTOR(S) : Steven Sablotsky, John M .Questel, and James A. Thompson

It is certified that error appears in the above-indentified patent and that said Letters Patent is hereby corrected as shown below:

| COLUMN | Line | |
|---|---|---|
| 12 | 47 | "Claim 1", should be --claim 16-- |

Signed and Sealed this

Eighth Day of July, 1997

Attest:

Bruce Lehman

BRUCE LEHMAN

*Attesting Officer*

*Commissioner of Patents and Trademarks*